(12) United States Patent
Forschner et al.

(10) Patent No.: US 6,191,321 B1
(45) Date of Patent: Feb. 20, 2001

(54) PROCESS FOR PREPARING 1,3-PROPANEDIOL FROM METHYL 3-HYDROXYPROPIONATE

(75) Inventors: Thomas Clayton Forschner, Richmond; Paul Richard Weider, Houston; Lynn Henry Slaugh, Houston; Joseph Broun Powell, Houston, all of TX (US)

(73) Assignee: Shell Oil Company, Houston, TX (US)

( * ) Notice: Under 35 U.S.C. 154(b), the term of this patent shall be extended for 0 days.

(21) Appl. No.: 09/163,534

(22) Filed: Sep. 30, 1998

(51) Int. Cl.$^7$ .................................................. C07G 27/04
(52) U.S. Cl. .......................................... 568/864; 568/861
(58) Field of Search ...................................... 568/861, 864

(56) References Cited

U.S. PATENT DOCUMENTS

| | | | |
|---|---|---|---|
| 1,746,783 | 2/1930 | Lazier . | |
| 1,964,000 | 6/1934 | Lazier | 260/156 |
| 2,060,880 | 11/1936 | Lazier | 260/156.5 |
| 4,072,726 | 2/1978 | Nychka et al. | 260/633 |
| 4,112,245 | 9/1978 | Zehner et al. | 568/864 |
| 4,232,170 | 11/1980 | Grey et al. | 560/179 |
| 4,393,251 | 7/1983 | Broecker et al. . | |
| 4,789,502 | 12/1988 | Slaugh | 260/413 |
| 4,837,365 | 6/1989 | Morel | 568/394 |
| 4,837,368 | 6/1989 | Gustafson et al. | 568/881 |
| 4,929,777 | 5/1990 | Irick, Jr. et al. | 568/864 |
| 4,973,741 | 11/1990 | Beavers | 560/179 |
| 5,011,806 | 4/1991 | Irick, Jr. et al. | 502/202 |
| 5,043,480 | 8/1991 | Beavers | 568/496 |
| 5,124,491 | 6/1992 | Fleckenstein et al. | 568/885 |
| 5,185,476 | 2/1993 | Gustafson | 568/831 |
| 5,475,159 | 12/1995 | Singleton et al. . | |

FOREIGN PATENT DOCUMENTS 301806   6/1927   (GB) .
168627   5/1991   (IN) .

OTHER PUBLICATIONS

Chemical Abstracts, vol. 92, No. 1, Jan. 7, 1980 (1980–01–07) Columbus, Ohio, U.S., Abstract No. 6230A, Y. Kawabata, et al., "Hydroesterification of Oxiraines Over Cobalt Carbonyl Catalysts," XP002125902 Abstract & Nippon Kagaku Kaishi, No. 5, 1979, pp. 635–640. (English Abstract).

International Search Report of Dec. 17, 1999.

"The Hydrogenation of Esters to Alcohols at 25–150°," by Homer Adkins and Harry R. Billica, *Journal of the American Chemical Society*, vol. 70, No. 9, Sep. 30, 1948, pp. 3121–3125.

"Hydrogenation of Esters to Alcohols Over Raney Nickel. I," Homer Adkins and Harry R. Billica, *Journal of the American Chemical Society*, vol. 69, No. 7, Jul. 22, 1947, pp. 3039–3041.

"The Preparation of Raney Nickel Catalysts and Their use Under Conditions Comparable With Those for Platinum and Palladium Catalysts," by Homer Adkins and Harry R. Billica, *Journal of the American Chemical Society*, vol. LXX, Jan.–Mar. 1948, pp. 695–698.

"Hydrogenation of Esters to Alcohols," *Organic Reactions*, vol. VIII, John Wiley & Sons, Inc., 1954, p. 9.

"The Preparation of Copper–Chromium Oxide Catalysts for Hydrogenation," Ralph Connor, Karl Folkers, and Homer Adkins, *Journal of the American Chemical Society*, vol. 54, No. 3, Mar. 1932, pp. 1138–1145.

(List continued on next page.)

*Primary Examiner*—Deborah Carr

(57) ABSTRACT

1,3-Propanediol is prepared in good yield by hydrogenation of methyl 3-hydroxypropionate in the presence of a copper zinc oxide hydrogenation catalyst. The use of the copper zinc oxide hydrogenation catalyst enables greater productivity in an overall process for preparing 1,3-propanediol from ethylene oxide via methyl 3-hydroxypropionate intermediate.

8 Claims, 1 Drawing Sheet

OTHER PUBLICATIONS

"Reductions: Selectivity," *Advanced Organic Chemistry, Third Edition*, John Wiley & Sons, Inc. 1985, pp. 1093–1096.

"Hydrogenation of Unsaturated Esters," by John Sauer and Homer Adkins, *Journal of the American Chemical Society*, vol. 59, No. 1, Jan. 11, 1937, p.p. 2–3.

"Effect of Ratio of Catalyst and Other Factors Upon the Rate of Hydrogenation," by Homer Adkins and Harry R. Billica, *Journal of the American Chemical Society*, vol. 70, No. 9, Sep. 30, 1948, pp. 3118–3120.

"Hydrogenolysis of Succinates and Glutarates," by Bruno Wojcik and Homer Adkins, *Journal of the American Chemical Society*, vol. LV, Sep.–Dec. 1933, pp. 4939–4946.

"Catalytic Hydrogenation of Amides to Amines," by Bruno Wojcik and Homer Akins, *Journal of the American Chemical Society*, vol. LVI, Jul.–Dec. 1934, pp. 2419–2424.

"Hydrogenolysis of β–Oxygenated Esters to Glycols," by Ralph Mozingo and Karl Folkers, *Journal of the American Chemical Society*, vol. LXX, Jan.–Mar. 1948, pp. 227–229.

"The Catalytic Hydrogenation of Esters to Alcohols II," by Karl Folkers and Homer Adkins, *Journal of the American Chemical Society*, vol. 54, No. 3, Mar., 1932, pp. 1145–1154.

"Hydrogenolysis of Oxygenated Organic Compounds," by Ralph Connor and Homer Adkins, *Journal of the American Chemical Society*, vol. 54, No. 9, Sep., 1932, pp. 4678–4690.

"Acid and Basic Catalysis," by J. N. Bronsted, *Chemical Reviews*, vol. V, No. 3, Sep., 1928, pp. 231–338.

"Studies on Ruthenium–Tin Boride Catalysts," by V. M. Deshpande, K. Ramnarayan, and C. S. Narasimhan, *Journal of Catalysis*, vol. 121, No. 1, Jan. 1990, pp. 174–182.

"Homogeneous Catalytic Hydrogenation of Carboxylic Acid Esters to Alcohols," by Roger A. Grey, Guido P. Pez, Andrea Wallo, and Jeff Corsi, *Journal of the Chemical Society, Chemical Communications*, No. 16/ 1980, pp. 783–784.

"The Reductive Carbonylation of Methanol With Homogenous Iron–Cobalt Catalysts," by Gerald Doyle, *Journal of Molecular Catalysis*, vol. 13, No. 2, Nov. 1981, pp. 237–247.

"The Catalytic Hydrocarbonylation of Alcohols—A Review," by M. E. Fakley and R. A. Head, *Applied Catalysis*, 5 (1983) pp. 3–18.

"The Catalytic Hydrogenation of Esters to Alcohols," by Homer Adkins and Karl Folkers, *The Journal of the American Chemical Society*, vol. LIII, Jan.–Apr. 1931, pp. 1095–1097.

PROCESS FOR PREPARING 1,3-PROPANEDIOL FROM METHYL 3-HYDROXYPROPIONATE

BACKGROUND OF THE INVENTION

This invention relates to the preparation of 1,3-propanediol. In one embodiment, the invention relates to a selective process for manufacturing 1,3-propanediol from ethylene oxide in which production of aldehyde intermediates is relatively low.

1,3-Propanediol is a starting material in the production of polyesters for fibers and films. It is known to prepare 1,3-propanediol in a two-step process involving (1) the cobalt-catalyzed hydroformylation (reaction with synthesis gas, $H_2/CO$) of ethylene oxide to intermediate 3-hydroxypropanal (HPA) and (2) hydrogenation of the HPA to 1,3-propanediol. One disadvantage of this route involves the tendency of the HPA intermediate to react with itself, resulting in the formation of intermediate by-products which do not undergo hydrogenation to the desired 1,3-propanediol product.

An alternate route to 1,3-propanediol from ethylene oxide involves production of intermediate methyl 3-hydroxypropionate followed by hydrogenation of the methyl 3-hydroxypropionate to 1,3-propanediol. This route would have the advantage of eliminating HPA and the associated by-products; however, this route is typically very unselective for 1,3-propanediol because of the tendency of the methyl 3-hydroxypropionate to undergo hydrogenolysis in the presence of ester hydrogenation catalysts such as copper chromium oxide or Raney nickel.

It is therefore an object of the invention to provide a selective, efficient process for hydrogenating methyl 3-hydroxypropionate to 1,3-propanediol. It is a further object of a specific embodiment of the invention to provide a selective process for the preparation of 1,3-propanediol via methyl 3-hydroxypropionate intermediate.

SUMMARY OF THE INVENTION

According to the invention, methyl 3-hydroxypropionate is hydrogenated to 1,3-propanediol in the presence of a copper zinc oxide hydrogenation catalyst.

According to one embodiment of the invention, 1,3-propanediol is prepared in a process comprising the steps of:
(a) contacting ethylene oxide with carbon monoxide and methanol in the presence of an effective amount of a carbonylation catalyst under methoxycarbonylation conditions, to produce an intermediate product mixture comprising methyl 3-hydroxypropionate;
(b) separating the methyl 3-hydroxypropionate from the intermediate product mixture and passing the methyl 3hydroxypropionate to a hydrogenation zone;
(c) contacting the methyl-3-hydroxypropionate with hydrogen in the presence of a copper zinc oxide hydrogenation catalyst under hydrogenation conditions to produce a hydrogenation product mixture comprising 1,3-propanediol; and
(d) recovering 1,3-propanediol from the hydrogenation product mixture.

The process enables the production of 1,3-propanediol in good yield and high selectivity in a process which avoids the problems inherent in producing an HPA intermediate.

DETAILED DESCRIPTION OF THE INVENTION

Figure 1:
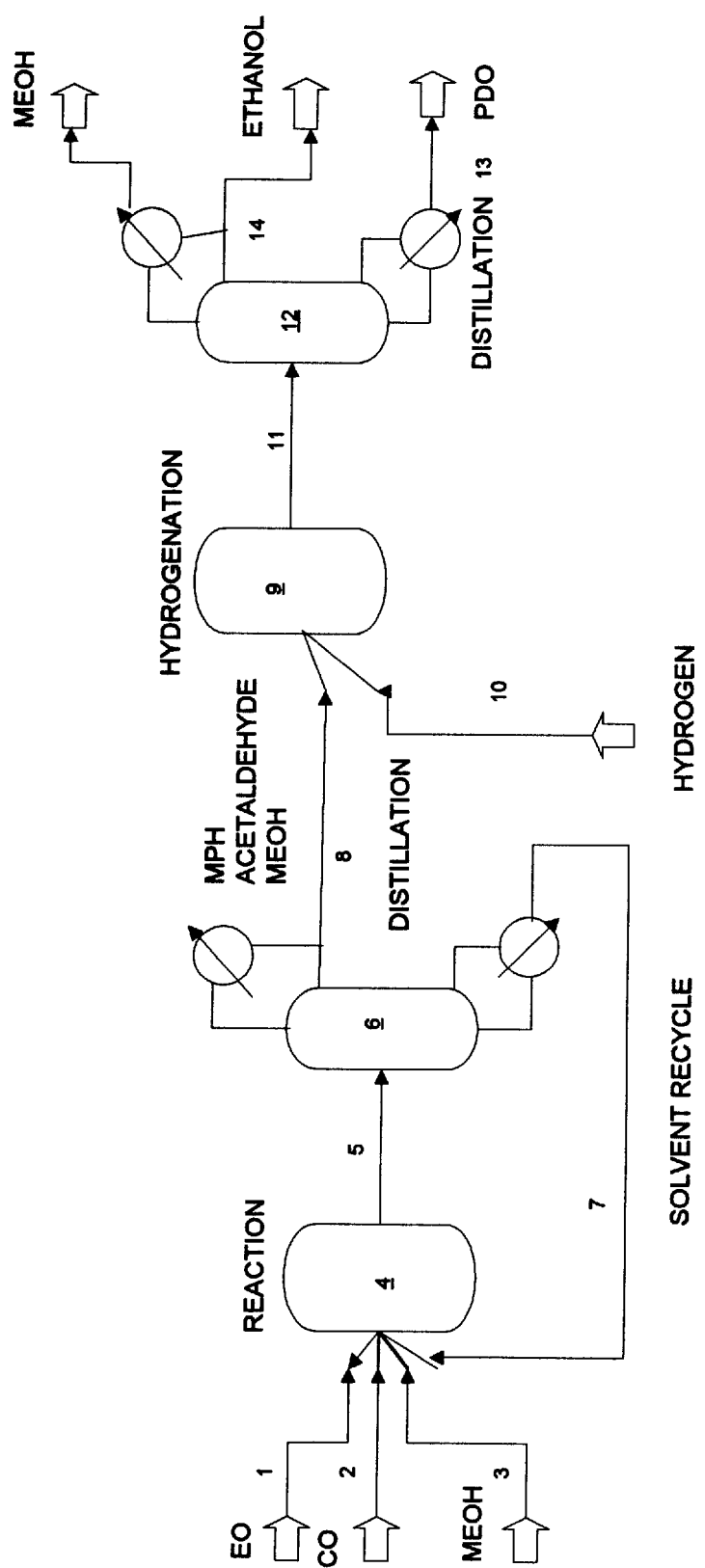
FIG. 1 is a schematic flow diagram of a preferred embodiment of the invention 1,3-propanediol preparation process.

According to the invention, methyl 3-hydroxypropionate is hydrogenated to 1,3-propanediol in the presence of a copper zinc oxide hydrogenation catalyst. The copper zinc oxide hydrogenation catalyst can be prepared as the bulk oxide or supported on a refractory material such as aluminum oxide. The bulk oxides are prepared by dissolving the precursor copper and zinc salts into an aqueous solution. The amount of zinc in the hydrogenation catalyst mixture is within the range of about 0.75 to about 5 moles, based on the moles of copper in the catalyst. The mixed metal salt solution is then added to a basic aqueous solution, such as ammonium carbonate to effect the precipitation of the mixed metal oxides from solution. The metal oxides are then isolated by filtration and dried to remove bulk water. Alternatively, the hydrogenation catalyst can be prepared by impregnating the aqueous mixed metal salts solution onto a refractory support, such as aluminum oxide, followed by drying to remove bulk water. The catalyst is optionally calcined in air or an inert atmosphere at elevated temperatures (200–400° C.). The catalyst is then cooled to room temperature and slowly heated under nitrogen to an elevated temperature (150–300° C.) to activate the catalyst.

The copper zinc oxide hydrogenation catalyst can be used in combination with a catalyst promoter to increase the rate and/or selectivity of the hydrogenation reaction. Suitable promoters include salts of lithium, sodium, potassium, magnesium, calcium, strontium, barium, titanium, zirconium, hafnium, and chromium. The current preferred hydrogenation catalyst promoter is a combination of barium and zirconium. The zirconium promoter is present in the hydrogenation catalyst in an amount within the range of about 0.0001 to about 0.1 mole percent, based on moles of copper in the hydrogenation catalyst. The barium promoter is present in the hydrogenation catalyst in an amount within the range of about 0.0001 to about 0.1 mole percent, based on the moles of copper in the hydrogenation catalyst.

The hydrogenation reaction is carried out at an elevated temperature within the range of about 130 to about 220° C., preferably about 150 to about 180° C., and under a hydrogen pressure of at least 100 psig, generally within the range of about 200 to about 2000 psig. Lower temperatures are generally preferred for greater selectivity.

The hydrogenation reaction is carried out in a liquid which is a solvent for the methyl 3-hydroxypropionate and does not interfere with the hydrogenation reaction. Suitable solvents include water, alkanols such as methanol, ethanol and isopropanol; aromatic compounds such as benzene and toluene; and others such as methyl-t-butyl ether, diphenyl ether, glyme, diglyme and dioxane.

In one embodiment of the invention, the above-described hydrogenation process is the second step of a two-step process for preparing 1,3-propanediol. In the first step, ethylene oxide, carbon monoxide and methanol are reacted to prepare the methyl 3-hydroxypropionate. Such a 1,3- propanediol preparation process can be conveniently described by reference to FIG. 1. Separate or combined streams of ethylene oxide 1, carbon monoxide 2 and methanol 3 are charged to reaction vessel 4, which can be a pressure reaction vessel such as a bubble column or agitated tank, operated batchwise or in a continuous manner. The feed streams are contacted in the presence of a carbonylation catalyst effective to promote the formation of the desired intermediate methyl 3-hydroxypropionate.

The methanol will generally be present in the reaction vessel in an amount within the range of about 1 to about 100 moles per mole of ethylene oxide.

The methoxycarbonylation reaction is carried out under conditions effective to produce a reaction product mixture containing a major portion of methyl 3-hydroxypropionate along with minor portions of 1,1-dimethoxy ethane, 2-methoxy ethanol and methyl(β-hydroxyethoxy) propionate. Generally, the reaction is carried out at an elevated temperature within the range of about 50 to about 120° C., most preferably about 60 to about 80° C., and at a carbon monoxide pressure within the range of about 500 to about 5000 psig, preferably (for process economics) about 1000 to about 3000 psig, with higher pressures preferred for greater selectivity.

A large number of carbonylation catalysts are known in the art, with preferred catalysts being those which promote the selective formation of methyl 3-hydroxypropionate under relatively mild carbonylation conditions of temperature and pressure. Suitable carbonylation catalysts include cobalt and rhodium carbonyls, optionally used in combination with a promoter. Although ligated cobalt and rhodium catalysts can be used, they are less preferred because of their greater cost and greater difficulty of recycle.

The currently preferred methoxycarbonylation catalyst is a non-phosphine-ligated cobalt carbonyl. The cobalt catalyst can be supplied to the methoxycarbonylation reactor in essentially any form including metal, supported metal, Raney-cobalt, hydroxide, oxide, carbonate, sulfate, acetylacetonate, salt of a carboxylic acid, or as an aqueous cobalt salt solution, for example. It may be supplied directly as a cobalt carbonyl such as dicobaltoctacarbonyl or cobalt hydridocarbonyl. If not supplied in the latter forms, operating conditions can be adjusted such that cobalt carbonyls are formed in situ via reaction with $H_2$ and CO, as described in J. Falbe, "Carbon Monoxide in Organic Synthesis," Springer-Verlag, NY (1970). In general, catalyst formation conditions will include a temperature of at least 50° C. and a carbon monoxide partial pressure of at least about 100 psig. For more rapid reaction, temperatures of about 120 to 150° C. should be employed, at CO pressures of at least 500 psig. Addition of high surface area activated carbons or zeolites, especially those containing or supporting platinum or palladium metal, can accelerate cobalt carbonyl formation from noncarbonyl precursors. The resulting catalyst is maintained under a stabilizing atmosphere of carbon monoxide, which also provides protection against exposure to oxygen. The most economical and preferred catalyst method involves heating a solution of a catalyst precursor to about 90 to about 120° C. under a carbon monoxide environment. For the preferred cobalt catalyst, the preferred catalyst precursor is cobalt hydroxide in methyl-t-butyl ether solvent.

The amount of cobalt present in the reaction mixture will vary depending upon the other reaction conditions, but will generally fall within the range of about 0.01 to about 1 wt %, preferably about 0.05 to about 0.3 wt %, based on the weight of the reaction mixture.

The methoxycarbonylation reaction mixture will preferably include a catalyst promoter to accelerate the reaction rate. Suitable promoters include dimethyldodecyl amine, sodium acetate, 1,10-phenanthroline, 2-hydroxypyridine and sodium methoxide.

It is generally preferred to maintain the concentration of water in the carbonylation reaction mixture at two percent or less, although higher levels can be tolerated.

Following the methoxycarbonylation reaction, reaction product mixture 5 containing methyl 3-hydroxypropionate, methanol, 1,3-propanediol, the cobalt catalyst and a minor amount of reaction by-products, is passed to distillation column (or liquid/liquid separator) 6 for separation and recycle via 7 of the methoxycarbonylation solvent and the carbonylation catalyst. Methyl 3-hydroxypropionate and methanol are removed overhead, cooled and passed via 8 to hydrogenation zone 9 and reacted with hydrogen 10 in the presence of a copper zinc oxide hydrogenation catalyst to produce a hydrogenation product mixture 11 containing 1,3-propanediol. The hydrogenation step may also revert some heavy ends to 1,3-propanediol.

1,3-Propanediol-containing product stream 11 is passed to distillation column 12 for recovery of 1,3-propanediol 13 and mixed alcohols 14.

EXAMPLE 1

Preparation of Hydrogenation Catalyst

To 150 ml of distilled water were added 10.5 g of barium nitrate and 6.0 g of zirconyl nitrate. The solution was gently heated until the salts dissolved. In a separate beaker, 120 g of copper nitrate and 192 g of zinc nitrate were dissolved into 250 ml of distilled water. These two solutions were then mixed together in a 2000 ml beaker. The solution was magnetically stirred while a 500 ml solution containing 192 g of ammonium carbonate was added dropwise via an addition funnel. The mixed oxides were isolated by filtration, washed with water, and dried over night at 150° C. The metal oxide catalyst was pressed at an isostatic pressure of 20,000 psi into a cake. The cake was sieved to a particle size of 12 to 30 mesh before loading into the hydrogenation reactor. The catalyst was heated to 400° C. at a rate of 5° C./min. under an air flow of 200 ml/min. The catalyst was cooled to room temperature and the air flow turned off. The catalyst was heated to 275° C. at a rate of 0.5° C./min. with hydrogen flowing over the catalyst at a rate of 130 ml/min.

EXAMPLE 2

Hydrogenation of Methyl 3-hydroxypropionate to 1,3-Propanediol

Methyl 3-hydroxypropionate was catalytically reduced in a flow reactor (0.5×17 in) in the presence of a copper zinc oxide catalyst under 1500 psi hydrogen. The flow rate of hydrogen through the reactor was controlled by the pressure differential across a 10-meter length of capillary tubing. The methyl 3-hydroxypropionate was dissolved in methanol and the solution was passed through the reactor at 25 mL/h. 35-ml samples of product were collected at 1 atm and 0° C. GC results (uncorrected) are shown in Table 1.

TABLE 1

CONVERSION AND 1,3-PROPANEDIOL (PDO) SELECTIVITIES FOR THE
HYDROGENATION OF METHYL 3-HYROXYPROPIONATE (MHP) OVER COPPER
ZINC HYDROGENATION CATALYST PROMOTED WITH BARIUM AND ZIRCONIUM

| Hydrogenation Conditions[1,2] | | $H_2$ Flow Rate | | | MHP | Selectivity % | | |
|---|---|---|---|---|---|---|---|---|
| Solvent | LHSV | cc/min | Press. | Temp. | Conv. % | 1-Propanol | Methyl Propionate | PDO % |
| MeOH | 1 | 230 | 1500 | 165 | 50.19 | 14.23 | 25.04 | 60.73 |
| MeOH | 1 | 230 | 1500 | 165 | 61.22 | 8.75 | 9.76 | 81.49 |
| MeOH | 1 | 230 | 1500 | 180 | 76.66 | 16.76 | 15.13 | 68.10 |
| MeOH | 1 | 230 | 1500 | 180 | 93.94 | 19.08 | 14.09 | 66.83 |
| MeOH | 1 | 230 | 1500 | 190 | 93.90 | 22.37 | 16.06 | 61.57 |
| MeOH | 1 | 230 | 1500 | 190 | 99.66 | 43.24 | 16.46 | 40.31 |

[1]Starting Feed:
Methanol 91.9 mole %
Methyl 3-hydroxypropionate 7.205 mol %
[2]Catalyst volume was 20 cc.

EXAMPLE 3

Methoxycarbonylation of Ethylene Oxide to Methyl 3-hydroxypropionate

In an inert atmosphere, a 100 ml parr autoclave was charged with 116 mg (0.33 mmole) of dicobalt octacarbonyl, 35 mg (0.2 mmole) of 1,10-phenanthroline, 4 g (123 mmole) of methanol and 27 ml of water saturated (1–2% wt.) methyl tert-butyl ether solvent. The autoclave was sealed and pressured to 500 psig with carbon monoxide and stirred at 90° C. Ethylene oxide (1.7 g, 39 mmole) was injected into the stirred mixture under carbon monoxide pressure and the pressure raised to 1125 psig. The reaction mixture was stirred for 18 hr. at 90° C. and then cooled to 15° C. and vented. Nitrogen-purged, deionized water (20 ml) was injected under an atmosphere of carbon monoxide and the mixture was stirred for 5 minutes and then allowed to stand for 10 minutes permitting the water and methyl tert-butyl ether phases to separate. The water layer was removed from the autoclave via syringe leaving the methyl tert-butyl ether phase in the autoclave. Gas chromatographic analysis of the water phase showed a selectivity of 74% to the desired product, methyl 3-hydroxypropionate and 26% to 1,1-dimethoxyethane with an 11% conversion of the ethylene oxide. Metal analysis of the methyl tert-butyl ether layer showed that it contained 1370 ppm cobalt.

To demonstrate the recyclability of the catalyst, methanol, 4 gm (123 mmole) was added to the autoclave containing the recovered methyl tert-butyl ether catalyst solution and the autoclave pressured to 500 psig with carbon monoxide and stirred at 90° C. Ethylene oxide, 1.9 g (43 mmole) was injected under carbon monoxide pressure and the pressure was raised to 1250 psig. The reaction mixture was stirred and heated at 90° C. for 18 hr., cooled to 15° C. and worked up with nitrogen-degassed, deionized water in an identical manner to the above procedure. Gas chromatographic analysis of the reaction products showed that there was 14% conversion of ethylene oxide with a 40% selectivity to methyl 3-hydroxypropionate and 60% to 1,1-dimethoxyethane. Analysis for cobalt gave 700 ppm cobalt in the water layer and 1020 ppm in the organic layer.

We claim:
1. In a process in which methyl 3-hydroxypropionate is hydrogenated to 1,3-propanediol in the presence of a hydrogenation catalyst, the improvement in which the hydrogenation catalyst comprises a catalytic amount of copper zinc oxide.

2. The process of claim 1 in which the hydrogenation process is carried out in an alkanol solvent.

3. The process of claim 1 in which the hydrogenation catalyst comprises a zirconium promoter.

4. The process of claim 1 in which the copper zinc oxide hydrogenation catalyst is present in an amount within the range of about 0.75 to about 5 moles per mole of copper in the hydrogenation catalyst.

5. The process of claim 3 in which the hydrogenation catalyst further comprises a barium promoter.

6. A process for preparing 1,3-propanediol comprising the steps of:
   (a) contacting, in a reaction zone, ethylene oxide with carbon monoxide and methanol in the presence of an effective amount of a carbonylation catalyst under methoxycarbonylation conditions of temperature and pressure to produce an intermediate product mixture comprising methyl 3-hydroxypropionate;
   (b) passing the intermediate product mixture to a separation zone, separating the methyl 3-hydroxypropionate from the intermediate product mixture, and passing the methyl 3-hydroxypropionate to a hydrogenation zone.
   (c) passing the methyl 3-hydroxypropionate to a hydrogenation zone and contacting the methyl 3-hydroxypropionate with hydrogen in the presence of a copper zinc oxide hydrogenation catalyst under sufficient conditions of temperature and pressure to provide a hydrogenation product mixture comprising 1,3-propanediol; and
   (d) recovering 1,3-propanediol from said hydrogenation product mixture.

7. The process of claim 6 in which the hydrogenation catalyst further comprises at least one of a zirconium and a barium promoter.

8. The process of claim 6 which further comprises passing the carbonylation catalyst from the separation zone to the reaction zone.

* * * * *